United States Patent [19]

Aspirot et al.

[11] Patent Number: 4,668,511
[45] Date of Patent: May 26, 1987

[54] PROCESS FOR THE BIOLOGICAL CONTROL OF INSECTS WHICH DESTROY CROPS, AND INSECTICIDAL COMPOSITIONS

[75] Inventors: Jacques Aspirot, Antony; Gerard Biache, D'Arcy; Robert Delattre, Paris; Pierre Ferron, Les Clayes vous Bois, all of France

[73] Assignees: Institut National de la Recherche Agronomique; National de Recherches du Coton et des Textiles Exotiques, both of Paris, France

[21] Appl. No.: 527,950

[22] Filed: Aug. 30, 1983

[30] Foreign Application Priority Data

Sep. 3, 1982 [FR] France .................. 82 15097

[51] Int. Cl.$^4$ .................. A01N 63/00; A01N 43/40
[52] U.S. Cl. .................. 424/93; 514/319; 514/320; 514/331
[58] Field of Search .................. 424/93; 514/319, 320, 514/331

[56] References Cited

U.S. PATENT DOCUMENTS 4,024,163  5/1977  Elliott et al. .................. 514/461
4,328,237  5/1982  Picarrdi et al. .................. 514/519 X
4,439,415  3/1984  Hennart et al. .................. 514/531 X

FOREIGN PATENT DOCUMENTS 1372957  11/1974  United Kingdom .

OTHER PUBLICATIONS

Jurkovicová et al., Virology; 93:8-19 (1979).
Chem Abst.; 90:181500q (1979).
Luttrell et al., *J. Econ. Ent.*, vol. 72, No. 1, pp. 57-60 (1979).
Biol. Abs., 69:15471 (1980).
Biol. Abs., 70:15563 (1980).
Biol. Abs., 70:43007 (1980).
Komolpith, *Biological Abstracts*, vol. 68, No. 11, 66607, Nov. 1979.
Wegler, "Chemie der Pflanzenschutz- und Schädlings-bekämpfungsmittel, vol. 7, pp. 10-16, 1981.

*Primary Examiner*—Esther M. Kepplinger
*Assistant Examiner*—Shawn P. Foley
*Attorney, Agent, or Firm*—Berman, Aisenberg & Platt

[57] ABSTRACT

The process consists in treating the crop conjointly with at least one baculovirus from *Spodoptera littoralis* or *Mamestra brassicae* and at least one photostable pyrethrinoid.

The insecticidal compositions comprises the combination of at least one of the said baculovirus and at least one photostable pyrethrinoid; doses of baculovirus and pyrethrinoid are advantageously below usual doses.

Such compositions and process are used to control noctuid Lepidoptera by potentiation of the viroses induced by nuclear polyhedra.

19 Claims, 1 Drawing Figure

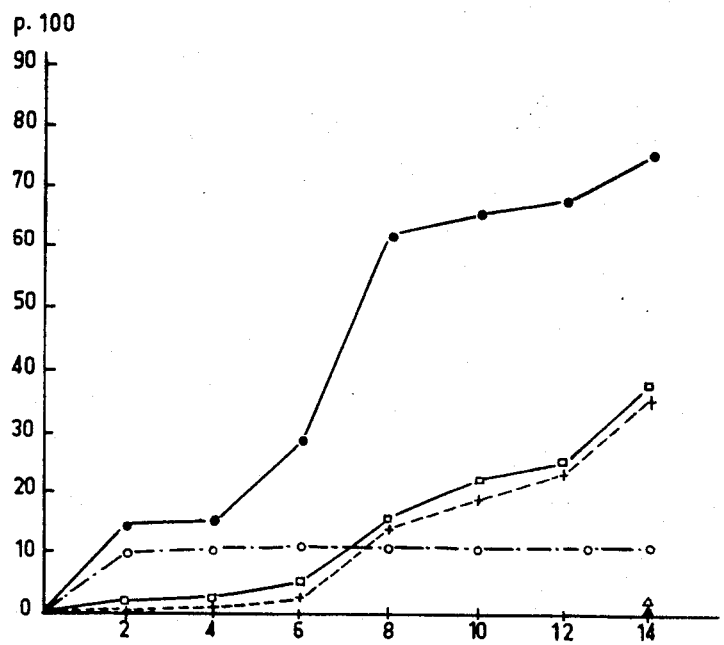

PROCESS FOR THE BIOLOGICAL CONTROL OF INSECTS WHICH DESTROY CROPS, AND INSECTICIDAL COMPOSITIONS

The present invention relates to the biological control of insects which destroy crops, and it relates more particularly to the potentiation of entomopathogenic microorganisms, in particular baculoviruses, using a synthetic chemical insecticide.

Entomopathogenic fungi, like entomopathogenic viruses and bacteria, are used to control insects which harm crops or insects which carry human disesases. In this respect, reference may be made to the following work: "Microbial Control of Pests and Plants Diseases, 1970–1980", edited by H. D. BURGES, Academic Press, 1981, 949 pages.

Multiplication of entomopathogenic viruses (baculoviruses) is achieved by the mass breeding of insects. However, the doses of inoculum to be used for biological control are too high to permit large-scale use of this method of control against insects which destroy crops.

Attempts have already been made to potentiate the infection caused by baculoviruses by using them in combination with insecticides. An example which may be mentioned is the article by KOMOLPITH and RAMAKRISHNAN in Journal of Entomological Research 2(1): 15–19 (1978), which relates to the potentiation of the virosis of the cotton pest *Spodoptera litura* (*Fabricius*) when a pyrethrin is used in combination with the virus inoculum.

The pyrethrins are natural insecticides extracted from plants belonging to the family of the compositae *Chrysanthemum tamrutense, C. carneum* and, in particular, *C. cinerareafolium*. They consist mainly of the esters of two acids: chrysanthemic acid or pyrethric acid, with three different alcohols. These natural pyrethrins are called Pyrethrin I or II, Jasmolin I or II and Cinerin I or II, the substances having the number I being chrysanthemic acid esters and the substances designated by the number II being pyrethric acid derivatives.

The pyrethrinoids, which are synthetic insecticides, are derivatives of the natural pyrethrins.

It will be noted that the majority of the pyrethrins and some synthetic pyrethrinoids are photodegradable. Consequently, their period of action is limited; however, it can be prolonged by using stabilizers. For example, U.S. Pat. No. 4,094,969 describes a pesticidal composition containing a photodegradable pesticide chosen from amongst pyrethrin, allethrin and microbial insecticides, and a stabilizer chosen from amongst catechols and leucocyanidines. The said patent does not describe specific compositions containing both a pyrethrin or allethrin and a microbial insecticide.

The use of the pyrethrinoids in agriculture could only really be developed after it was known how to make them photostable, in particular by the introduction of halogen radicals and phenoxybenzyl alcohol (see French Pat. No. 73/18,983 published under No. 2,185,612 in the name of NATIONAL RESEARCH DEVELOPMENT CORP.) and also by virtue of the development of industrial synthesis processes.

R. G. LUTTRELL et al., in Journal of Economic Entomology, Volume 72, No. 1, 1979, pages 57–60, proposed the use of a baculovirus inoculum, the *Heliothis baculovirus*, in combination with various chemical insecticides, in particular with a pyrethrinoid, namely permethrin. These authors did not observe a synergy phenomenon with a combination of this type.

French Pat. No. 72/36,367, published under U.S. Pat. No. 2,156,348, describes pesticidal compositions containing, as the active ingredient, a mixture consisting of one or more types of effective ingredients from microorganisms belonging to the genus Bacillus, and of one or more types of synthetic pyrethroid insecticides. The Bacillus in question are *Bacillus thuringiensis, Bacillus moritai* and *Bacillus popilliae*.

It has now been found, surprisingly, that it is possible to potentiate the viroses caused by certain baculoviruses by using the inocula of these baculoviruses in combination with at least one photostable pyrethrinoid, the baculoviruses being those originating from the insects *Spodoptera littoralis* and *Mamestra brassicae*.

These baculoviruses have formed the subject of several fundamental studies, which have enabled them to be characterized. The following studies may be mentioned as examples:

for the baculovirus from *Mamestra brassicae*:

M. JURKOVICOVA, L. VAN TOUM, S. S. SUSSENBACH and J. TER SHEGGET, in Virology, Volume 93, 1979, pages 8–19.

J. VLAK and A. GRONER, in Journal for Invertebrate Pathology, Volume 35, 1980, pages 269–278.

for the baculovirus from *Spodoptera littoralis*:

N. KISLEV, H. EDELMAN and I. HARPAZ, in Journal for Invertebrate Pathology, Volume 17, 1971, pages 199–202.

A. MERDAN, Liliane CROIZIER, J. C. VEYRUNES and G. CROIZIER, in Entomophaga, Volume 22, 1977, pages 413–420.

The strains of the two baculoviruses which were used in the experiments described below were isolated in the laboratories of the Institut National de la Recherche Agronomique (INRA) [National Institute of Agronomy Research (NIAR)] and deposited in the Collection Nationale de Cultures de Microorganismes [National Collection of Microorganism Cultures] at the Institut Pasteur (PARIS) on 1st September 1982 under the following numbers:

I-203 for the baculovirus from *Spodoptera littoralis*
I-204 for the baculovirus from *Mamestra brassicae*.

Thus, the present invention relates to a process for the biological control of insects which destroy crops, essentially the noctuid lepidoptera, by potentiation of the viroses with nuclear polyhedra, which consists of treating the crop conjointly with at least one baculovirus chosen from amongst those originating from the insects *Spodoptera littoralis* and *Mamestra brassicae* and with at least one photostable pyrethrinoid.

The present invention also relates to an insecticide composition comprising at least one baculovirus chosen from amongst those originating from *Spodoptera littoralis* and *Mamestra brassicae*, in combination with at least one photostable pyrethrinoid.

With a combination of this type, a synergistic phenomenon has been observed which is characterized by a potentiation of the virosis in the host insect *Spodoptera littoralis* or *Mamestra brassicae*.

Furthermore, with the baculovirus from *Mamestra brassicae*, a potentiation of the virosis has also been observed on the insects *Heliothis virescens, Spodoptera littoralis* or, *Spodoptera frugiperda, Diparopsis watersi, Earias insulana, Pectinophora gossypiella, Crypstophlebia leucotreta* and the like.

The compounds of formula I are examples of photostable pyrethrinoids which are suitable for the purposes of the invention:

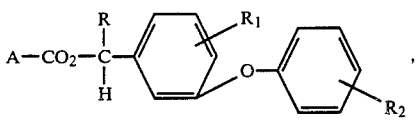

in which R represents a hydrogen atom, an alkyl radical containing from 1 to 4 carbon atoms, an alkynyl radical containing from 2 to 8 carbon atoms or a group —C≡N, $R_1$ and $R_2$ both represent a hydrogen atom or one of them represents a hydrogen atom and the other a fluorine or chlorine atom, and (a) either A represents a radical

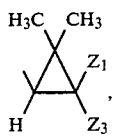

in which: either $Z_1$ and $Z_2$ each represent a methyl radical or $Z_1$ represents a hydrogen atom and either $Z_2$ represents a radical

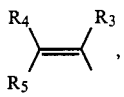

in which $R_3$ represents a hydrogen or halogen atom and $R_4$ and $R_5$, which are identical or different, represent a halogen atom or an alkyl radical containing from 1 to 8 carbon atoms, or together form a cycloalkyl radical containing from 3 to 6 carbon atoms or a radical

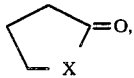

in which the ketone is in the α-position relative to the double bond and in which X represents an oxygen or sulfur atom or a radical NH, or $Z_2$ represents a radical

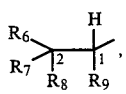

in which $R_6$, $R_7$, $R_8$ and $R_9$, which are identical or different, each represent a halogen atom, (b) or A represents a radical

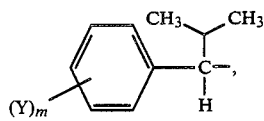

in which Y, in any position on the benzene nucleus, represents a hydrogen atom, a halogen atom, an alkyl radical containing from 1 to 8 carbon atoms or an alkoxy radical containing from 1 to 8 carbon atoms and m represents the number 0, 1 or 2, in all their possible isomeric forms or in the form of mixtures of isomers.

If R represents an alkyl radical, it is preferably the methyl or ethyl radical.

If R represents an alkynyl radical, it is preferably the ethynyl radical.

If $R_3$ represents a halogen atom, it is preferably a chlorine or bromine atom.

If $R_4$ and $R_5$ both represent halogen atoms, they preferably both represent chlorine atoms, bromine atoms or fluorine atoms.

$R_6$, $R_7$, $R_8$ and $R_9$ preferably represent chlorine or bromine atoms.

If Y, $R_4$ and $R_5$ represent alkyl radicals, they are preferably methyl, ethyl, isopropyl, n-butyl or t-butyl radicals.

If Y represents a halogen atom, it is preferably a chlorine atom.

If Y represents an alkoxy radical, it is preferably the methoxy group.

Amongst these photostable pyrethrinoids which are suitable for the purposes of the invention, the compounds below, for which the international common name (ICN) has also been indicated, will be noted in particular:

| ICN | Photostable pyrethrinoid |
|---|---|
| deltamethrin | S—α-cyano-3-phenoxybenzyl 1R—cis-2,2-dimethyl-3-(2,2-dibromovinyl)-cyclopropanecarboxylate |
| cypermethrin | R,S—α-cyano-3-phenoxybenzyl d,l-cis/trans-2,2-dimethyl-3-(2,2-dichlorovinyl)-cyclopropane-1-carboxylate (cis/trans: 30/10) |
| cypermethrin HI cis | R,S—α-cyano-3-phenoxybenzyl d,l-cis/trans-2,2-dimethyl-3-(2,2-dichlorovinyl)-cyclopropane-1-carboxylate (containing 90% of cis) |
| cyfluthrin | d,l-α-cyano-(3-phenoxy-4-fluorophenyl)-methyl d,l-cis/trans-2,2-dimethyl-3-(2,2-dichlorovinyl)-cyclopropanecarboxylate |
| fenvalerate | S—α-cyano-3-phenoxybenzyl 2-para-chlorophenyl-2-isopropylacetate |
| flucitrinate | d,l-α-cyano-3-phenoxybenzyl d,l-2-(4-difluoromethoxyphenyl)-2-isopropylacetate |
| tralomethrin | S—α-cyano-3-phenoxybenzyl 1R—cis-(2,2,2-tribromo-1-bromoethyl)-2,2-dimethylcyclopropanecarboxylate |
| tralocythrin | S—α-cyano-3-phenoxybenzyl 1R—cis-(2,2-dichloro-1,2-dibromoethyl)-2,2-dimethylcyclopropanecarboxylate |

Preferably, a reduced dose of pyrethrinoid is used according to the invention.

According to the present invention, "reduced dose" denotes a dose smaller than that recommended for application to the ground.

As regards the baculovirus, the dose usually recommended for application to the ground is about $10^{13}$ polyhedra per hectare.

Field trials on cotton crops, carried out by using the baculovirus from *Mamestra brassicae* in combination with deltamethrin, made it possible to demonstrate the synergism of this combination, taking the cottonseed yield as the criterion. In fact, the combination of a dose of deltamethrin in the range of 1/5 to 1/15, and particularly of 1/10 of the normally recommended dose (25 g of active ingredient/ha) with a dose of a baculovirus inoculum from *Mamestra brassicae* of $1.10^{13}$ or $10^{12}$ polyhedra/ha resulted in a significant increase in the cottonseed yield, compared with the same products used separately at the same doses, in case of crops infested with caterpillars of Lepidoptera with endo or exocarpic life. Field trials on cotton crops, infested with caterpillars of Lepidoptera with exocarpic life, particularly Heliothis or Spodoptera demonstrate the synergism in the efficacity of the combination of the baculovirus from *Spodoptera littoralis*, at a dose normally prescribed or even at a minor dose, with a photo-stable pyrethrinoid, for example deltamethrin, at a lower dose than normally prescribed, particularly 1/5, said combination being applied on the field at usual periodicity, i.e. 14 days, or less.

Potentiation of the virosis was also demonstrated in the laboratory by the biological test technique on the insects taken as targets. This biological test technique consists in subjecting batches of carterpillars, at a known stage of development, to infection with increasing doses of baculovirus or to intoxication with increasing doses of pyrethrinoids.

In practice, it is advantageous to breed the insects and to carry out the tests on an artificial nutrient medium, the composition of which is given by POITOUT and BUES in Les Annales de Zoologie et d'Ecologie Animale, Volume 2, pages 79–91, 1970, for the two species in question, namely: *Mamestra brassicae* and *Spodoptera littoralis*.

The experiments are carried out on caterpillars at the L1 stage before ecdysis, 30 caterpillars being used per batch and each experimental variant being carried out 8 times. The different doses of baculovirus tests are intimately mixed with the nutrient medium while it is being made up, at the moment when the temperature of the medium reaches 50° C. during its cooling stage. The ratios of the amounts of polyhedra to the volume of nutrient medium are then taken and expressed as the number of polyhedra per $mm^3$. These various doses of baculovirus can also be deposited on the surface of the nutrient medium using a micropipette, in the same way as the various doses of pyrethrinoid; the amounts of baculovirus and active ingredient are then expressed respectively as polyhedra/$mm^2$ and ml/$mm^2$.

The insects are then bred on this contaminated nutrient medium, in individual compartments, in a climatically controlled enclosure, at 25±1° C. and an RH of 75±5% and with a period of illumination of 17 hours out of 24. The mortality is checked every day.

The results obtained make it possible to establish the equations of the regression lines for logarithm of the dose of polyhedra vs.probit value of the mortality, and for logarithm of the dose of pyrethrinoid vs.probit value of the mortality, and these equations are used to calculate the 50% lethal doses using the techniques described by P. LAZAR in: Les essais biologiques ["Biological assays"] published by CESAM, 1976.

These laboratory tests also showed that potentiation was obtained with a reduced dose of pyrethrinoid and a reduced dose of baculovirus.

For example, potentiation of the virosis was obtained in the laboratory for concentrations of the baculovirus isolated from *Spodoptera littoralis* of between about LD 50 and LD 30 when using deltamethrin as the pyrethrinoid in amounts of between about LD 10 and LD 20.

Likewise, if the baculovirus used is that which has been isolated from *Mamestra brassicae* and the pyrethrinoid is deltamethrin, the appropriate doses are as follows:

baculovirus from *Mamestra brassicae* at doses of between about LD 50 and LD 20, for example of between LD 20 and LD 30, deltamethrin at doses of between about LD 10 and LD 20.

It will be recalled that the abbreviation "LD 50" is the 50% lethal dose, that is to say the dose which causes a 50% mortality of the insects by application of the product in question. Likewise, the LD 30, LD 20 and LD 10 are the lethal doses which cause a mortality of 30%, 20% and 10% respectively.

The lethal doses indicated above for the pyrethrinoid correspond in practice to 1/80 of the dose normally recommended for field applications, which is 25 g of active ingredient per hectare in the case of deltamethrin.

In general, it is pointed out that the doses of pyrethrinoids which are preferred for the purposes of the invention are doses in the range from 1/5 to 1/100 the normal dose recommended for the compound in question, taking account of the application conditions in the laboratory and in the field.

For the baculoviruses, the lethal doses indicated above correspond approximately to values of between 1/5 and 1/10 of the dose normally used.

Thus, according to the invention, it is possible to use the baculovirus in amounts less than or equal to the amount normally recommended ($10^{13}$ polyhedra/ha).

The compositions according to the invention can be presented in the form of powders, granules, suspensions, emulsions, solutions, solutions for aerosols, baits or other preparations conventionally employed for the use of insecticides.

Apart from the active principles, these compositions generally contain a carrier and/or a non-ionic surface-active agent, which additionally ensures a uniform dispersion of the constituent substances of the mixture. The carrier used can be a liquid, such as water, alcohol, hydrocarbons or other organic solvents or a mineral, animal or vegetable oil, or a powder such as talc, clay, silicate or keiselguhr.

If appropriate, one or more additional pesticides can be incorporated into the compositions according to the invention.

As a variant, the active principles according to the invention can be applied successively to the crops to be treated; it will be noted, however, that simultaneous application is more advantageous. The active principles according to the invention can therefore also be packaged separately, for example in the form of wettable powders in the case of the baculoviruses and in the form of emulsifiable concentrates in the case of the photostable pyrethrinoids. The compositions according to the invention are then obtained by mixing the active ingredients in the presence of one of the abovementioned diluents, in amounts appropriate to the characteristics of the treatment apparatus used and of the crop to be protected.

Examples of compositions according to the invention are given below:

| 1st composition according to the invention | |
|---|---|
| S—α-cyano-3-phenoxybenzyl 1R—cis-2,2-dimethyl-3-(2,2-dibromovinyl)-cyclopropane-1-carboxylate (deltamethrin)* | 2.5 g/liter |
| preparation of polyhedra containing | 50 g/liter |

| | |
|---|---|
| 1.6.10$^{12}$ polyndedra of baculovirus originating from Spodoptera littoralis | |
| "Atlox" 4851 (1) | 0.040 g/liter |
| "Atlox" 4855 (2): | 0.035 g/liter |
| xylene | 947.425 g/liter |
| 2nd composition according to the invention | |
| S—α-cyano-3-phenoxybenzyl 1R—cis-2,2-dimethyl-3-(2,2-dibromovinyl)-cyclopropane-1-carboxylate (deltamethrin)* | 3 g/liter |
| preparation of polyhedra containing 5.10$^{12}$ polyhedra of baculovirus originating from Mamestra brassicae | 150 g/liter |
| "Atlox" 4851 (1) | 0.040 g/liter |
| "Atlox" 4855 (2) | 0.035 g/liter |
| xylene | 846.925 g/liter |
| 3rd composition according to the invention | |
| S—α-cyano-3-phenoxybenzyl 1R—cis-2,2-dimethyl-3-(2,2-dibromovinyl)-cyclopropane-1-carboxylate (deltamethrin)* | 3 g/liter |
| preparation of polyhedra containing 1.10$^{13}$ polyhedra of baculovirus originating from Spodoptera littoralis | 300 g/liter |
| "Emcol H 300 B" (3) | 0.1 g/liter |
| "Emcol H 500 B" (3) | 0.1 g/liter |
| xylene | 696.8 g/liter |

(1) Oxyethyleneated triglyceride combined with a sulfonate, of acid value 1.5.
(2) Oxyethyleneated triglyceride combined with a sulfonate, of acid value 3.0.
(3) Calcium salt of an alkylbenzenesulfonate combined with polyoxyethyleneated ethers.
*The deltamethrin used in these compositions is the product known by the tradename DECIS, in which the concentration of deltamethrin active ingredient is 25 g/liter.

The doses indicated above therefore correspond approximately to 1/10 of the normal dose.

In view of the polyphagia of the target pests, which are essentially Noctuid lepidoptera, the field of application of the process of the invention covers not only cotton crops, but also soya, rice, maize, beet, tobacco, the various market-garden crops including tomatoes, cabbages and beans, fodder crops, such as alfafa and Egyptian clover, and also vines, citrus fruits, tea, mulberries, coffee, bananas and similar crops which can be effected by Noctuid Lepidoptera.

Tests have shown that potentiation is not obtained with all entomopathogenic viruses, but specifically with the two baculoviruses from Spodoptera littoralis and Mamestra brassicae. On the other hand, no potentiation is obtained with the most widely studied baculoviruses, such as the baculovirus from Lymantria dispar, the baculovirus from Autographa californica and the baculovirus from Heliothis sp. (Elcar). Surprisingly, a very high specificity of the compositions according to the invention has therefore been observed.

The invention will now be described in greater detail by means of the examples below:

EXAMPLE 1

Demonstration of the phenomenon of potentiation of the virosis, with nuclear polyhedra, of the noctuid Lepidoptera Spodoptera Littoralis following simultaneous contamination with its own baculovirus and with a reduced dose of deltamethrin.

The experiment performed was of the complete block type carried out eight times using 30 individuals per batch.

Six variants were carried out in order to demonstrate the potentiation with the composition according to the invention.

These variants are as follows:
untreated control
deltamethrin
parathion-methyl
baculovirus from Spodoptera littoralis
baculovirus from Spodoptera littoralis+deltamethrin
baculovirus from Spodoptera littoralis+parathion-methyl.

First of all, the 50% lethal dose (LD 50) were determined for each product taken in isolation; these lethal doses are as follows:

1.2 polyhedra per mm$^3$ of nutrient medium used to feed the caterpillars 2.10$^{-9}$ ml per mm$^2$ of the commercial product based on deltamethrin 1.25.10$^{-6}$ mg per mm$^2$ of the commerical product based on parathion-methyl.

The doses actually used to determine the potentiation of the compositions according to the invention were as follows:

0.6 polyhedron per mm$^3$ for the baculovirus (=LD 30)

1.25.10$^{-9}$ ml per mm$^2$ of deltamethrin (=LD 10)

8.10$^{-7}$ mg per mm$^2$ of parathion-methyl (=LD 1).

The polyhedra were intimately mixed with the nutrient medium at 50° C. before the latter was gelled; the chemical insecticides, on the other hand, were deposited on the surface using a micropipette.

The insects subjected to the experiment were caterpillars of Spodoptera Littoralis, at the L1 stage before ecdysis, bred individually on the artificial nutrient medium corresponding to that described by POITOUT and BUES (Ann. Zool. Ecol. Anim. 1970, 2: 79-91), but enriched with powdered cabbage (0.8 g per 100 g of medium) and with benzoic acid (0.125 g per 100 g of medium).

After treatment of the nutrient medium, the insects were deposited in individual plastic compartments placed on the medium, and bried in a climatically controlled enclosure, at a temperature of 25°±1° C. and a relative humidity of 75±5%, with a period of illumination of 17 hours out of 24.

The state of health was then checked every two days up to the sixth larval stage, the mortality being taken as the criterion of efficacy of the treatment.

Comparison of the average cumulative mortalities obtained for each experimental variant is made by applying DUNCAN's multiple range test.

The overall results are shown in FIG. 1, which represents the activity, as a function of time, of the chemical insecticides deltamethrin and methyl-parathion, of the biopreparation of baculovirus from Spodoptera littoralis, and of their combination. The abbreviations used on the curves in this figure have the following meanings: (B+MP=baculovirus+methyl-parathion; B+D=baculovirus+deltamethrin; D=deltamethrin; B=baculovirus; C=control; MP=methyl-parathion). Thus, in this figure, the days have been plotted on the abscissa and the percentage mortality on the ordinate. No mortality was observed in the control batch. The efficacy of the treatment with the chemical insecticides used by themselves is zero or low, the cumulative mortality after 14 days of observation being at most 11% for the deltamethrin variant. The baculovirus by itself causes a mortality of 36%, this value being similar to that obtained with the same amount of polyhedra used in combination with the reduced dose of parathion-methyl; on the other hand, the mortality reaches 76% when the virus is combined with the reduced dose of deltamethrin. Table I below collates the averages obtained with the various combinations. Statistical analysis shows particularly that the difference in activity between the combination "baculovirus+deltamethrin" and all the other experimental variants is highly significant at the 1% level. On the other hand, the combination "baculovirus+parathion-methyl" is the same as the variant with baculovirus by itself, at the 5% level.

simultaneous contamination of caterpillars of the lepidoptera Haliothis armigera with its own baculovirus and a reduced dose of deltamethrin

| | |
|---|---|
| deltamethrin at 1/100 of the strength of the commercial preparation | 47% |
| baculovirus from *Heliothis armigera*, containing 0.2 polyhedron/mm² | 27% |
| deltamethrin + baculovirus | 11% |

TABLE 1

| Multiple comparison of the average cumulative mortalities (DUNCAN's test) | | | | | | | |
|---|---|---|---|---|---|---|---|
| | Parathion-methyl 3.71 | Control 5.60 | Deltamethrin 18.94 | Baculovirus 37.43 | Baculovirus + parathion-methyl 38.47 | Baculovirus + deltamethrin 62.21 | Delta 5% | Delta 1% |
| Parathion-methyl | 3.71 | 1.89 | 15.23* | 33.72** | 34.76** | 58.50** | 14.199 | 19.505 |
| Control | 5.60 | 0 | 13.34 | 31.83** | 32.87** | 56.61** | 14.013 | 19.238 |
| Deltamethrin | 18.94 | | 0 | 18.49* | 19.53** | 43.27** | 13.750 | 18.883 |
| Baculovirus | 37.43 | | | 0 | 1.04 | 24.78** | 13.370 | 18.392 |
| Baculovirus + parathion-methyl | 38.47 | | | | 0 | 23.74** | 12.752 | 17.635 |
| Baculovirus + deltamethrin | 62.21 | | | | | 0 | | |

*The result obtained is significant at the 5% level
**The result obtained is significant at the 1% level According to the definitions proposed by BENZ (1971, Microbial Control of Insects and Mites, Academic Press, London, edited by H. D. BURGES and H. W. HUSSEY, 327-355), the phenomenon demonstrated in the experiments described above is a synergy with potentiation of the virosis.

EXAMPLE 2

Experiment with the baculovirus from *Mamestra brassicae*.

Following the same procedure as in Example 1, caterpillars of the lepidoptera *Mamestra brassicae* were contaminated simultaneously with the baculovirus from this lepidoptera and a reduced dose of deltamethrin. By way of comparison, the contamination was also carried out using deltamethrin by itself or the baculovirus by itself.

The results obtained are as follows:

| | |
|---|---|
| deltamethrin at 1/100 of the strength of the commercial preparation | 0% |
| baculovirus from *Mamestra brassicae*, containing 100 polyhedra per mm³ of medium | 22% |
| deltamethrin + baculovirus (at the same doses) | 46% |

These results show that there is potentiation of the virosis with the combination deltamethrin+baculovirus from *Mamestra brassicae*.

EXAMPLE 3

Demonstration of the specificity of the compositions of the invention.

The same procedure was followed with other baculoviruses and it was found that there was no potentiation of the virosis of the type observed with *Spodoptera littoralis* and *Mamestra brassicae*.

simultaneous contamination of caterpillars of the lepidoptera Lymantria dispar with its own baculovirus and a reduced dose of deltamethrin

| | |
|---|---|
| deltamethrin at 1/100 of the strength of the commercial preparation | 2% |
| baculovirus from Lymantria, containing 1 polyhedron/mm² | 10% |
| deltamethrin + baculovirus, containing 1 polyhedron/mm² | 9% | simultaneous contamination of caterpillars of Heliothis virescens with its own baculovirus (ELCAR) and a reduced dose of deltamethrin

| | |
|---|---|
| deltamethrin at 1/80 of the strength of the commercial preparation | 38% |
| baculovirus from Heliothis, containing 0.2 polyhedron/mm² | 19% |
| deltamethrin + baculovirus | 36% |

EXAMPLE 4

Use of different pyrethrinoids in the composition, according to the invention, based on the baculovirus from *Spodoptera littoralis*.

The procedure followed was substantially as described in Example 1, with the following compounds:

| | |
|---|---|
| series No. 1 | |
| deltamethrin at 1/80 | 19% |
| cypermethrin at 1/80 | 4% |
| cypermethrin HI-CIS at 1/80 | 9% |
| baculovirus from *Spodoptera littoralis* | 28% |
| baculovirus + deltamethrin | 64% |
| baculovirus + cypermethrin | 58% |
| baculovirus + cypermethrin HI-CIS | 59% |
| series No. 2 | |
| flucitrinate at 1/80 | 0% |

| | |
|---|---|
| cyfluthrin at 1/80 | 7% |
| baculovirus from Spodoptera littoralis | 34% |
| baculovirus + flucitrinate | 36% |
| baculovirus + cyfluthrin | 69% |
| series No. 3 | |
| deltamethrin at 1/80 | 0% |
| fenvalerate at 1/80 | 7% |
| flucitrinate at 1/80 | 3% |
| cyfluthrin at 1/80 | 3% |
| baculovirus of Spodoptera littoralis | 47% |
| baculovirus + deltamethrin | 60% |
| baculovirus + fenvalerate | 60% |
| baculovirus + flucitrinate | 27% |
| baculovirus + cyfluthrin | 44% |

Conclusion: the potentiation of the baculovirus from Spodoptera littoralis applied to caterpillars of Spodoptera littoralis in the presence of reduced doses of the different commercial pyrethrinoids is also demonstrated.

EXAMPLE 5

Broadening of the host spectrum of the baculovirus from Mamestra brassicae.

The procedure of Example 1 was followed, with caterpillars other than those of Mamestra brassicae. The results obtained are given below together with the doses used:

| | |
|---|---|
| on caterpillars of Spodoptera frugiperda | |
| deltamethrin at 1/80 | 57% |
| baculovirus from Mamestra, containing 40 polyhedra/mm$^2$ | 20% |
| baculovirus + deltamethrin (at the same doses) | 93% |
| on caterpillars of Heliothis armigera | |
| deltamethrin at 1/80 | 24% |
| baculovirus from Mamestra, containing 0.4 polyhedron/mm$^2$ | 11% |
| baculovirus + deltamethrin (at the same doses) | 20% |
| on caterpillars of Heliothis virescens | |
| deltamethrin at 1/100 | 18% |
| baculovirus from Mamestra, containing 4 polyhedra/mm$^2$ | 45% |
| baculovirus from Mamestra + deltamethrin (at the same doses) | 87% |
| on caterpillars of Spodoptera littoralis | |
| deltamethrin at 1/100 | 53% |
| baculovirus from Mamestra, containing 1,000 polyhedra/mm$^2$ | 8% |
| baculovirus + deltamethrin (at the same doses) | 59% |
| on caterpillars of Spodoptera exigua | |
| deltamethrin at 1/100 | 46% |
| baculovirus from Mamestra, containing 0.1 polyhedron/mm$^2$ | 11% |
| baculovirus from Mamestra + deltamethrin (at the same doses) | 57% |
| baculovirus from Mamestra, containing 0.4 polyhedron/mm$^2$ | 11% |
| baculovirus from Mamestra + deltamethrin (at the same doses) | 71% |
| on caterpillars of Ostrinia nubilalis | |
| deltamethrin at 1/80 | 13% |
| baculovirus from Mamestra, containing 1,000 polyhedra/mm$^2$ | 0% |
| baculovirus from Mamestra + deltamethrin (at the same doses) | 23% |
| on caterpillars of Lymantria dispar | |
| deltamethrin at 1/100 | 2% |
| baculovirus from Mamestra, containing 28,000 polyhedra/mm$^2$ | 15% |
| baculovirus from Mamestra + deltamethrin (at the same doses) | 8% |

The baculovirus from Mamestra brassicae is potentiated by deltamethrin in insects other than its host of origin, namely: the lepidoptera Spodoptera frugiperda, Spodoptera exigua and Heliothis virescens. This potentiation does not occur on Heliothis armigera, Spodoptera littoralis, Ostrinia nubilalis and Lymantria dispar.

EXAMPLE 6

Field trial.

The trial was carried out in a plantation, using 6 test areas each comprising 7 plots. Each individual plot consists of 8 rows of cotton 20 meters long. The 6 test areas are as follows:

A: untreated control

B: baculovirus from Mamestra, containing $10^{13}$ polyhedra/ha

C: deltamethrin at 1/10 of the normal dose, that is to say 0.1 liter of deltamethrin/ha D: combination of baculovirus and deltamethrin at 1/10 of the normal dose E: deltamethrin at the normal dose, that is to say 1 liter of deltamethrin/ha F: combination of baculovirus and deltamethrin at the normal dose.

Test areas, B, C, D and F received 12 applications of products at a rate of 1 treatment per week; test area E received 6 applications at a rate of 1 treatment per fortnight. The analysis related to the yields of cottonseed ($Y_1$, $Y_2$ and $Y_3$), starting from the crude data, taking account of the 3 harvesting periods. The results obtained are shown in Table II below. The caterpillars from the capsule Heliothis armigera and Diparopsis watersi caused substantial damage, especially to the first harvest. The test areas are classified according to DUNCAN's test at the 0.05 significance level.

TABLE II

| | Yields in kg/ha of cottonseed | | |
|---|---|---|---|
| | $Y_1$ | $Y_1 + Y_2$ | $Y_1 + Y_2 + Y_3$ |
| A: Untreated control | 180.5 c | 421.6 d | 619.4 d |
| B: Baculovirus from Mamestra | 212.8 c | 440.0 d | 658.1 d |
| C: Deltamethrin at 1/10 of the normal dose | 475.5 b | 992.1 c | 1,285.4 c |
| D: Deltamethrin at 1/10 + baculovirus | 598.3 ab | 1,147.9 b | 1,459.3 b |
| E: Deltamethrin at the normal dose | 612.1 ab | 1,206.1 ab | 1,513.2 ab |
| F: Deltamethrin at the normal dose + baculovirus | 725.0 a | 1,314.8 a | 1,660.2 a |

(a, b, c, d): the values followed by the same letter are not significantly different from one another.

We claim:

1. An insecticidal composition comprising a combination of (a) photostable synthetic insecticidal pyrethrinoid and (b) a member selected from the group consisting of *Spodoptera littoralis* baculovirus and *Mamestra brassicae* baculovirus, the amount of (a) being sufficient to potentiate insecticidal activity of (b) for controlling *Noctuid lepidoptera.*

2. An insecticidal composition of claim 1 which comprises baculovirus of *Spodoptera littoralis.*

3. An insecticidal composition of claim 1 which comprises baculovirus of *Mamestra brassicae.*

4. A composition as claimed in claim 1, wherein the photostable pyrethrinoid is a compound of formula I:

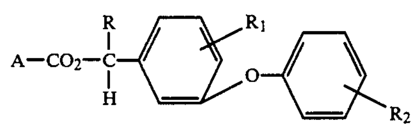

, (I)

wherein

R is a hydrogen, an alkyl radical with from 1 to 4 carbon atoms, an alkynyl radical with from 2 to 8 carbon atoms or —CN;

one of $R_1$ and $R_2$ is a hydrogen atom and the other is a member selected from the group consisting of a hydrogen atom, a fluorine atom and a chlorine atom;

A is a radical of one of the formulae 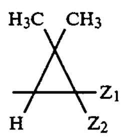 and

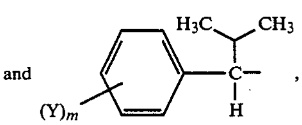

, each of $Z_1$ and $Z_2$ is a methyl radical or $Z_1$ is a hydrogen atom and $Z_2$ is a radical of one of the formulae 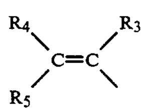 and

, $R_3$ is a hydrogen atom or a halogen atom;

each of $R_4$ and $R_5$ is, independently, a halogen atom or an alkyl radical with from 1 to 8 carbon atoms or $R_4$ and $R_5$, together with the carbon atom to which each is bound, form a cycloalkyl radical with from 3 to 6 carbon atoms or a radical of the formula

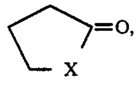

, in which the keto is in the α-position relative to the double bond;

X is an oxygen or sulfur atom or the radical —NH;

each of $R_6$, $R_7$, $R_8$ and $R_9$ is, independently, a halogen atom;

Y, in any position on the benzene nucleus, is a hydrogen atom, a halogen atom, an alkyl radical with from 1 to 8 carbon atoms or an alkoxy radical with from 1 to 8 carbon atoms and m is one of the numbers 0, 1 or 2;

or an isomer thereof.

5. A composition according to claim 1 wherein A is

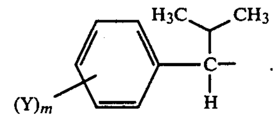

.

6. A composition according to claim 4 wherein A is the radical

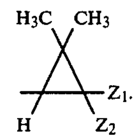

.

7. A composition according to claim 6 wherein $Z_2$ is

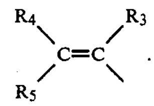

.

8. A composition according to claim 6 wherein $Z_2$ is

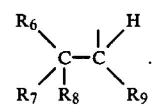

.

9. A composition as claimed in claim 8, wherein the photostable pyrethrinoid is a member selected from the group consisting of S-α-cyano-3-phenoxybenzyl 1R-cis-2,2-dimethyl-3-(2,2-dibromovinyl)-cyclopropanecarboxylate, R,S-α-cyano-3-phenoxybenzyl d,l-cis/trans-2,2-dimethyl-3-(2,2-dichlorovinyl)-cyclopropane-1-carboxylate (cis/trans: 30/10), R,S-α-cyano-3-phenoxybenzyl d,l-cis/trans-2,2-dimethyl-3-(2,2-dichlorovinyl)-cyclopropane-1-carboxylate (containing 90% of cis), d,l-α-cyano-(3-phenoxy-4-fluorophenyl)-methyl d,l-cis/trans-2,2-dimethyl-3-(2,2-dichlorovinyl)-cyclopropanecarboxylate, S-α-cyano-3-phenoxybenzyl 2-para-chlorophenyl-2-isopropylacetate, d,l-α-cyano-3-phenoxybenzyl d,l-2-(4-difluoromethoxyphenyl)-2-isopropylacetate, S-α-cyano-3-phenoxybenzyl 1R-cis-(2,2,2-tribromo-1-bromoethyl)-2,2-dimethylcyclopropanecarboxylate and S-α-cyano-3-phenoxybenzyl 1R-cis-(2,2-dichloro-1,2-dibromoethyl)-2,2-dimethylcyclopropanecarboxylate.

10. A process for biological control of *Noctuid lepidoptera,* which are crop-destroying insects, which comprises potentiating nuclear polyhedrosis virus infections of said insects by applying to the crop and/or insects a combination of a photostable insecticidal synthetic pyrethrinoid and a member selected from the group consisting of *Spodoptera littoralis* baculovirus and *Mamestra brassicae* baculovirus, the photostable pyrethrinoid being applied in an amount lower than that required for the chemical control of *Noctuid lepidoptera* by the pyrethrinoid alone and/or the baculovirus being applied in an amount lower than that required for the biological control of *Noctuid lepidoptera* by the baculovirus alone the combination being a synergistic combination in the process.

11. A process as claimed in claim 10, wherein the photostable pyrethrinoid is applied in an amount lower than that required for the chemical control of *Noctuid lepidoptera* by the pyrethrinoid alone.

12. A process as claimed in claim 11, wherein the baculovirus is applied in an amount lower than that required for the biological control of *Noctuid lepidoptera* by the baculovirus alone.

13. A process for biologically controlling insects which destroy crops which comprises applying to the insects and/or crops a combination of an amount of (a) photostable insecticidal synthetic pyrethrinoid together with an amount of (b) baculovirus selected from the group consisting of *Spodoptera littoralis* baculovirus and *Mamestra brassicae* baculovirus, the amount of (a) being sufficient to potentiate insecticidal activity of (b) with regard to said insects so that the combination is a synergistic combination in the process.

14. A process according to claim 13, wherein the amount of (a) is sufficient to potentiate synergistically the insecticidal activity of (b) for controlling *Noctuid lepidoptera*.

15. A process as claimed in claim 13, wherein the pyrethrinoid is S-α-cyano-3-phenoxybenzyl 1R-cis-2,2-dimethyl-3-(2,2-dibromovinyl)-cyclopropanecarboxylate, R,S-α-cyano-3-phenoxybenzyl d,l-cis/trans-2,2-dimethyl-3-(2,2-dichlorovinyl)-cyclopropane-1-carboxylate (cis/trans: 30/10), R,S-α-cyano-3-phenoxybenzyl d,l-cis/trans-2,2-dimethyl-3-(2,2-dichlorovinyl)-cyclopropane-1-carboxylate (containing 90% of cis), d,l-α-cyano-(3-phenoxy-4-fluorophenyl)methyl d,l-cis/-trans-2,2-dimethyl-3-(2,2-dichlorovinyl)cyclopropanecarboxylate, S-α-cyano-3-phenoxybenzyl 2-parachlorophenyl-2-isopropylacetate, d,l-α-cyano-3-phenoxybenzyl d,l-2-(4-difluoromethoxyphenyl)-2-isopropylacetate, S-α-cyano-3-phenoxybenzyl 1R-cis-(2,2,2-tribromo-1-bromoethyl)-2,2-dimethylcyclopropanecarboxylate or S-α-cyano-3-phenoxybenzyl 1R-cis-(2,2-dichloro-1,2-dibromoethyl)-2,2-dimethylcyclopropanecarboxylate.

16. A process as claimed in claim 15, wherein *Mamestra brassicae* baculovirus is applied at a dose less than or equal to $10^{13}$ polyhedra per hectare, and wherein the pyrethrinoid is applied at doses in the range from 1/5 to 1/100 of the normally recommended dose.

17. A process as claimed in claim 13, wherein the baculovirus is applied at a dose less than or equal to $10^{13}$ polyhedra per hectate, and wherein the pyrethrinoid is deltamethrin applied at a dose in the range of from 1/5 to 1/100 of the amount normally recommended for application to crops when used as sole insecticide.

18. A process as claimed in claim 17, wherein the insects comprise a member selected from the group consisting of *Spodoptera littoralis, Mamestra brassicae, Spodoptera frugiperda, Spodoptera exigua, Heliothis virescens, Diparopsis watersi, Earias insulana, Pectinophora gossypiella* and *Cryptophlebia leucotreta*.

19. A process as claimed in claim 13, wherein the insects comprise a member selected from the group consisting of *Spodoptera littoralis, Mamestra brassicae, Spodoptera frugiperda, Spodoptera exigua, Heliothis virescens, Diparopsis watersi, Earias insulana, Pectinophora gossypiella* and *Cryptophelebia leucotreta*.

* * * * *